United States Patent [19]

Propper

[11] Patent Number: 5,004,422
[45] Date of Patent: Apr. 2, 1991

[54] ORAL ENDOSTEAL IMPLANTS AND A PROCESS FOR PREPARING AND IMPLANTING THEM

[76] Inventor: Robert H. Propper, 401 N. Garfield, Alhambra, Calif. 91801

[21] Appl. No.: 435,073
[22] Filed: Nov. 9, 1989
[51] Int. Cl.⁵ .............................................. A61C 8/00
[52] U.S. Cl. .................................. 433/175; 433/201.1
[58] Field of Search ..................... 433/175, 201.1, 174, 433/173

[56] References Cited

U.S. PATENT DOCUMENTS

| | | | |
|---|---|---|---|
| 470,332 | 3/1892 | Friel | 433/175 |
| 2,857,670 | 10/1958 | Kiernan, Jr. | 433/175 |
| 3,576,074 | 4/1971 | Gualt | 433/175 |
| 3,628,248 | 12/1971 | Kroder | 433/201.1 |
| 3,979,828 | 9/1976 | Taylor | 433/175 |
| 4,773,858 | 9/1988 | Marquez | 433/175 |

Primary Examiner—Cary E. Stone
Attorney, Agent, or Firm—Donald D. Mon

[57] ABSTRACT

A process for preparing and implanting endosteal implants, and the implant used for the process. A tooth is extracted leaving a socket wall behind, which remains suitably fresh for a sufficient period of time. Promptly after extraction, a model is made of at least the major portion of the tooth. A replica is made of titanium or of a material having the property of osseointegration. While the socket is still suitably fresh, the replica is inserted the socket in surface to surface contiguity with a substantial area of the socket wall so as to provide an osseointegrated implant.

9 Claims, 3 Drawing Sheets

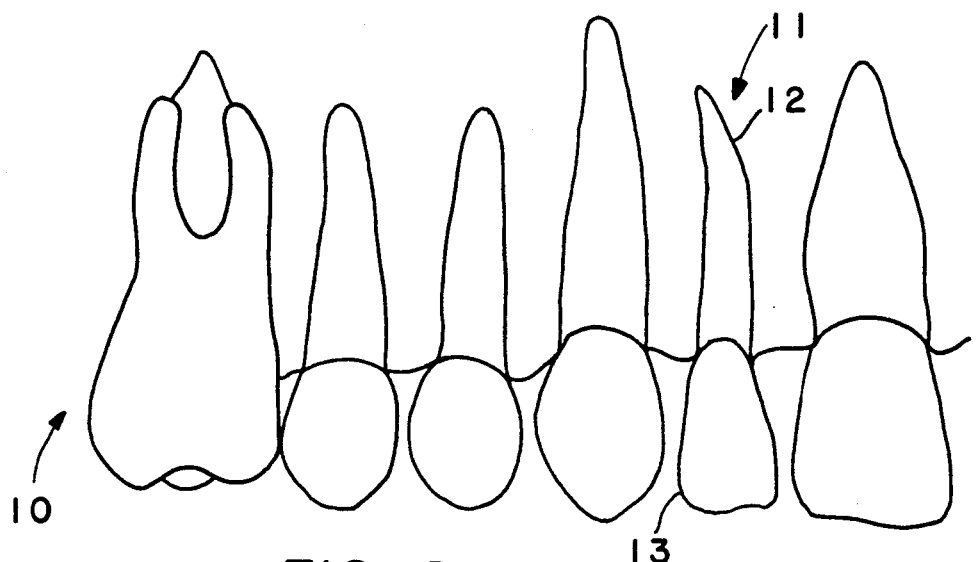
FIG. 2
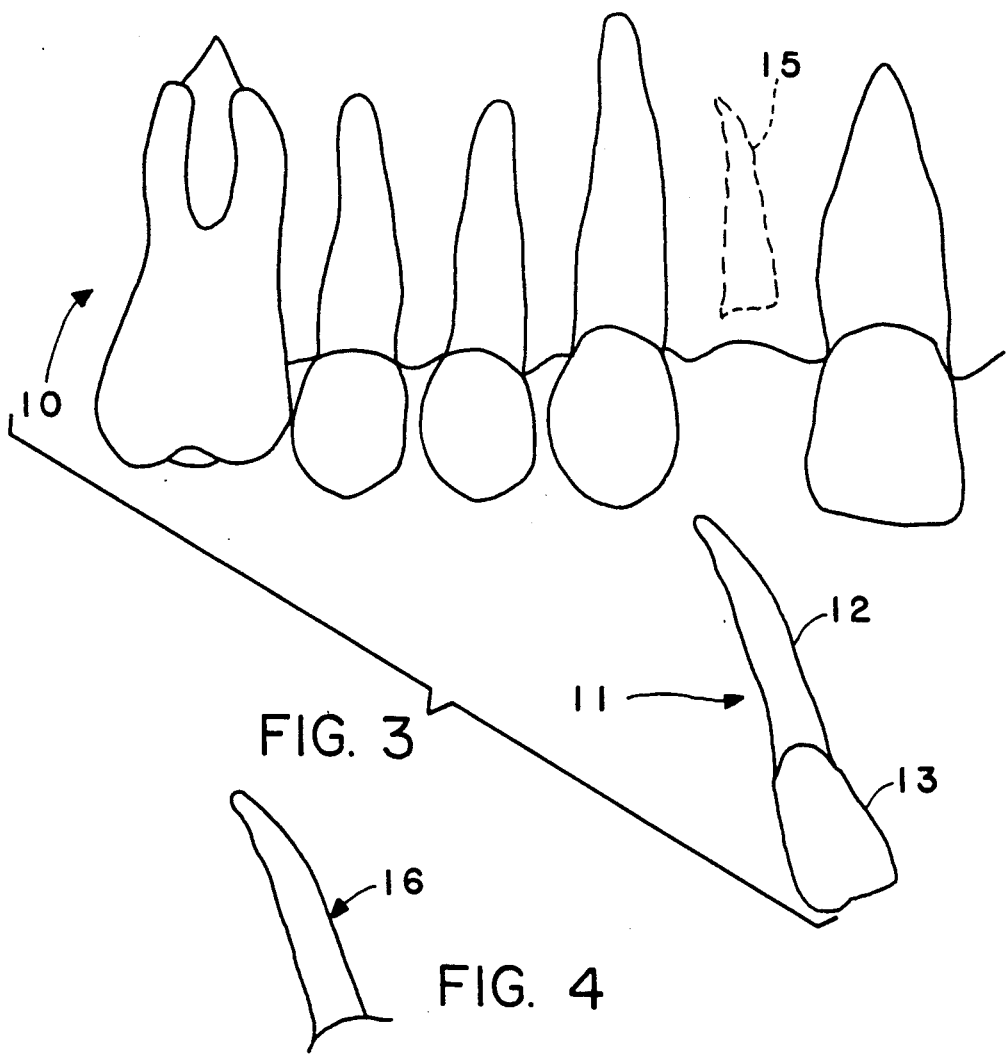
FIG. 3
FIG. 4

ORAL ENDOSTEAL IMPLANTS AND A PROCESS FOR PREPARING AND IMPLANTING THEM

FIELD OF THE INVENTION

This invention relates to oral endosteal implants, and to a process for preparing and implanting them.

BACKGROUND OF THE INVENTION

Oral implants, after literally centuries of failed efforts, have at last achieved such a degree of success that restoration of functions by means of implants is now a matter of reasonable expectation in a large percentage of patients who have lost teeth. The techniques vary widely, and can generally be categorized in two types: subperiosteal and endosteal.

The subperiosteal implant surmounts the bony structure, with posts rising from it to which a crown or other structure can be attached. The objective of the mounting means is to become attached to the bone, or to be held to the bone by tissue overgrowth. While this type of implant does have some successes, its potential for success, and applicability to many operation conditions are inferior to the potential of the endosteal implant.

The endosteal implant is intended to be inserted into the bony structure, and to be held there by ingrowth of tissue, by osseointegration with the bony structure itself, or by the use of screws or other self-retaining attachment means somehow physically engaged to the bony structure. There have been some considerable successes with endosteal implants, but as they generally exist in the art, their utility is often limited, especially where the bone has been severely reduced.

The inventor in this instant invention has devised a process and an implant which enables an endosteal implant to fit very closely in a natural socket in the jaw, and to be made of a material which is known to result in osteointegration, namely the firm integration of the implant in the bony structure without need for retention means such as expansion bolts, or the like. There results a firmly retained implant with least trauma to the patient, and which becomes as one with the bony structure.

At the present time, there are only two known substances which will be integrated with bony structure: titanium metal and hydroxylapetite. The knowledge that titanium will be osseointegrated has been developed by Branemark, and is now generally accepted. It has led to significantly greater acceptance of oral implants as a conventional practice. Other metals such as gold, and alloys such as vitallium, have had lesser success, and are not believed to be osseointegrated, although they are tolerated by the body.

A body coated with a suitably adherent layer of hydroxylapetite (hereinafter referred to as "HA"), will be retained by osseointegration with the layer of HA. However, should that layer somehow vanish, an implant not made of titanium will suffer the same fate as an implant which was not coated with HA. however, and HA-coated metal implant made of material other than titanium using the process of this invention is intended to be within the scope of this invention.

The known osseointegration of titanium is now so well-established, that prudent practitioners will prefer its use. It can readily be cast in centrifugal casting machines operating in an argon atmosphere. Such machines are in existence, as is sufficiently pure titanium.

It is another object of this invention to provide an implant made of a material which will osseointegrate in a shape corresponding to that of a natural socket in the jaw, and to implant it while the socket is suitably fresh, whereby to return to the socket an implant quite closely corresponding to the structure —a tooth —which was removed from it.

The idea of replacing an extracted tooth with a cast duplicate has been suggested by Kroder in U.S. Pat. No. 3,628,248. In this patent, Kroder concluded that metal implants could not be used in such a procedure because of the long time it would take to make the implant. By then, he concluded, a membrane he considered necessary to a successful implantation would have disappeared. For this reason, he cast a duplicate of the tooth in a resin and quickly implanted the resinous material. Not only was this material unacceptable, but his basic premise was incorrect. The membrane is largely destroyed anyway when the tooth is extracted. Whatever function it may have had in place with the original tooth, it would not have served for the resin implant. Kroder's procedure has not, to this inventor's knowledge, ever been generally accepted or even used beyond whatever experiments Kroder may have conducted.

When a tooth is first extracted, there remains in the jaw a socket formed of a bony structure most of whose internal surfaces are geometrically similar to the corresponding surfaces of the extracted tooth. In the course of the healing process, a blood clot will form in the socket, and then the blood clot will be invaded by other substances which gradually replace the clot. Then the shape of the surrounding socket structure will begin to change as the materials harden and the shapes are lost. This process takes substantial time, and it appears that no major change of socket shape occurs in the first two weeks after extraction. During this time, when the socket is considered "suitably fresh" for this procedure, the material in the socket can simply be removed with a curette to expose the bony structure. Within this initial period of time, whose maximum length is not presently known, a suitably shaped implant can be pressed into the socket with assurance that it will make surface-to-surface contact with bony structure over an area which, when osseointegrated, will be sufficient to support the implant.

It is not necessary and it cannot be expected to occur, that there will result a 100% area contact of tooth and socket. In fact, it will often be desirable to trim off some roots before making the casting to facilitate later insertion of the implant into the socket. A full area contact of about 30% is believed to be sufficient, and more will obviously be better. At areas where this contact is not made, the interstitial spacing will soon be filled with the same substances as the body provides to heal the socket in normal practice, and does no harm even if it does little good.

Accordingly, it is an object of this invention to provide an endosteal implant which closely conforms to a socket and which will be osseointegrated. This is done without further drilling or structural modification of the socket, and constitutes an important advantage over implants of a specific, often cylindrical, shape, which are implanted in a hole drilled to very close dimensions.

BRIEF DESCRIPTION OF THE INVENTION

This invention is a procedure subsequent to the extraction of a tooth. Promptly after the extraction of the tooth, a mold is made of it. The surgeon can, if he desires, trim off roots which project in ways that may make later insertion of the implant more difficult. Then using conventional molding practices, usually the lost-wax process, a suitably shaped heat-resistant mold is developed for making a replica of at least part of the tooth.

Thereafter a casting is made. If titanium is the material, it will normally be case in a centrifugal die-casting machine in an argon atmosphere. If some other metal is to be used, it will be case in accordance with conventional methods, and then coated with HA.

The resulting implant is then brought to the patient within the period of time when the socket remains suitably fresh. The socket is cleaned out by curettement, and the implant is pressed into the socket, taking good care that it is accurately fitted and with as much surface-to-surface contiguity with bony structure as is possible. Then over a period of time a suitable portion of the surface area of the implant will be osseointegrated, and the patient can anticipate a strong and useful replacement for his lost tooth.

It is not necessary to replicate the entire tooth, and often it will not be. The duplication is necessary only for that part of the tooth which fits in bony structure. Customarily one would form at least the root, and perhaps add to it above the root a post to receive a crown, if a total duplication of the tooth in titanium is not aesthetically desirable, as it will rarely be.

The above and other features of this invention will be fully understood from the following detailed description and the accompanying drawings, in which:

BRIEF DESCRIPTION OF THE DRAWINGS

FIG. 2 is a schematic showing of a group of teeth, one of which is to be extracted;

FIG. 3 shows the extraction, the extracted tooth, and the socket;

FIG. 4 shows a titanium replica (implant) of the root of the extracted tooth;

DETAILED DESCRIPTION OF THE INVENTION

Figure 1:
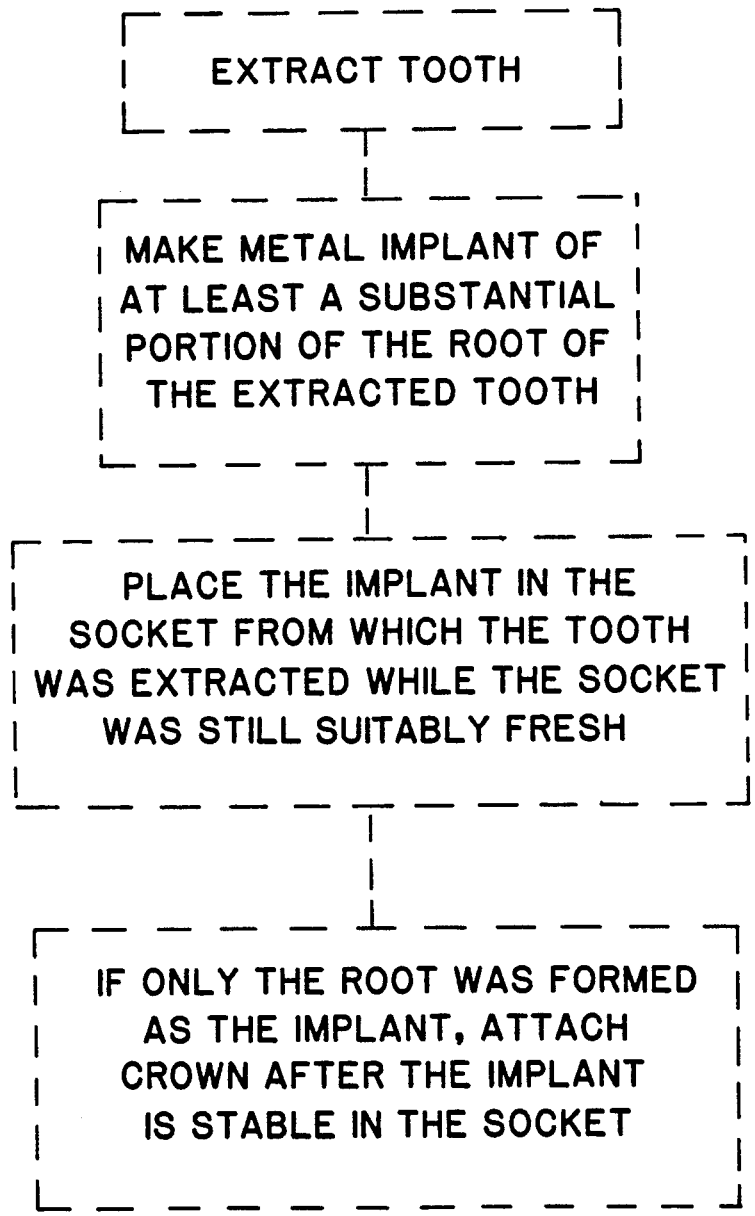
FIG. 1 is a flow chart showing the process of this invention.

FIG. 2 shows a row 10 of teeth. One tooth 11 is to be extracted. It is shown with a single root 12 and a crown 13.

FIG. 3 shows tooth 11 extracted, leaving behind a socket 15 in the jaw.

If desired, the entire tooth can be replicated, but more often only the root will be replicated. For this reason, FIG. 3 shows an implant 16 formed only as the root, the crown having been removed. Instead, the entire tooth could have been replicated, or the crown portion modified to form a post later to receive a crown.

Figure 5:
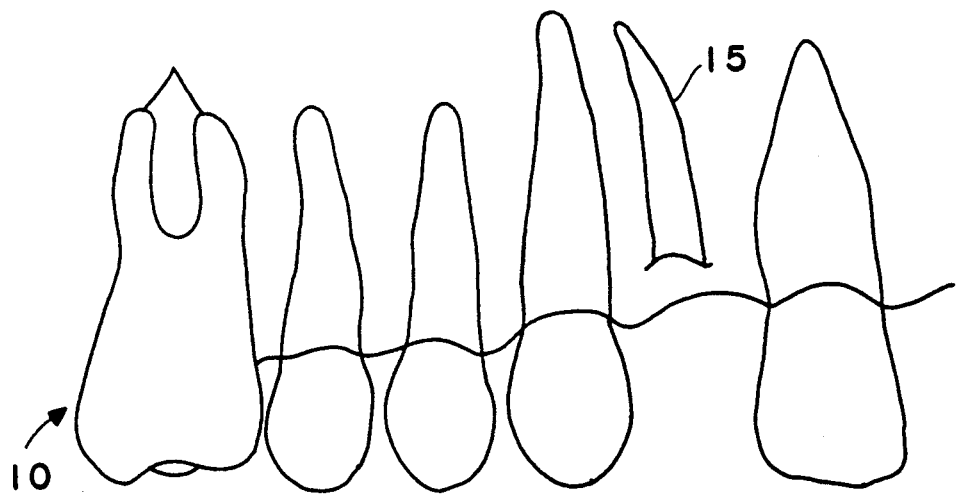
FIG. 5 shows the implant placed in the socket.

Whatever the situation, implant 16 is shown in FIG. 5 as having been pressed into the cleaned-out socket in the maximum surface-to-surface contiguity possible. The procedure is now suspended to await suitable fixation of the root in the socket. This may take as short a time at 1–2 months, or as long a time as 8–9 months.

When the root has become suitably stabilized, crown 20 can be attached to it, and the extracted tooth will have had its function replaced.

Figure 7:
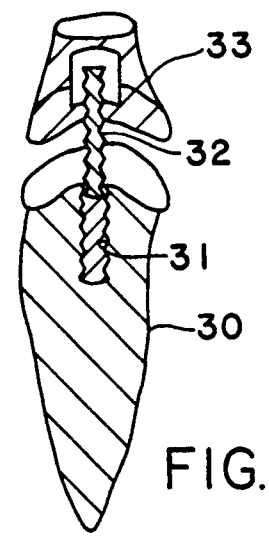
FIG. 7 shows another means of attaching a crown to the implant.

FIG. 7 shows an implant 30 as previously described with a threaded bore 31 to receive the threaded end of a headed screw 32 that passes through a post or crown 33 to hold the post or crown to the root.

Figure 8:
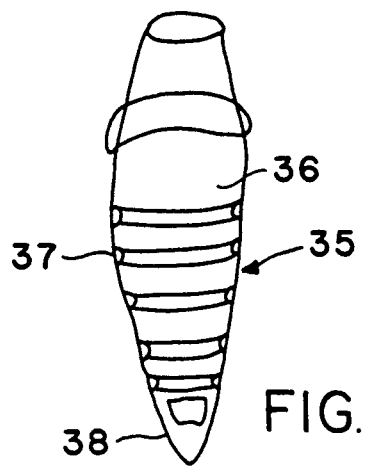
FIG. 8 shows a useful modification of the surface of the implants.

FIG. 8 shows a modification of an implant 35, which is generally like the implant of FIG. 4, except that its surface 36 has a plurality of grooves 37 formed in it. The objective is for ingrowth to engage in the grooves, the better to retain the implant. Also, a cross-port 38 is formed, so bone or tissue can pass through it the better to anchor the implant.

The implant preferably will be made of very pure titanium metal. Instead it may be made of any metal not rejected by the body and which is coated with HA. The layer of HA is very thin, and is not amenable to proportional illustration in the drawing.

The maximum length of time the socket remains suitably fresh is not known, and may never be, because patients will be impatient to receive their implants, and prudent practitioners will want to take the full advantages of the promptest possible implantation. At least two weeks are certainly available, and with presently-existing facilities it appears that the implants can be prepared within one week, and possible sooner as casting facilities become more available.

This invention thereby provides a process for implantation, and an implant suitable for use in this process which is expected to provide to the patient an oral implant which equals, and may even exceed, the properties and function of the extracted tooth.

Because the procedure uses the socket already present in the jaw, it is necessary to sacrifice bone to accommodate the implant such as by boring a hole or tapping a thread. Thus, whatever remained of structural integrity in the jaw will continue to be used in the implanted system. Nerve damage which can happen with other endosteal implants will be avoided. Sinus problems which are encountered with other endosteal implants are avoided.

This invention is not to be limited by the embodiments shown in the drawings and described in the description, which are given by way of example and not of limitation, but only in accordance with the scope of the appended claims.

I claim:

1. The process of providing an endosteal implant for the human jaw, comprising the following steps in the order recited:

a. extracting a tooth to leave a socket for later reception of an endosteal implant, said socket having a socket wall and the property of remaining suitably fresh for a sufficient period of time;

b. promptly after its extraction, preparing a model of at least the major portion of the root of said extracted tooth;

c. from said model preparing an implant comprising a replica of said model, said implant having an outer surface made of material having the property of osseointegration with bony structure forming said socket;

d. within the period of time the socket remains suitably fresh, removing material from said socket which has accumulated since the extraction, and exposing the bony structure forming said socket wall without significant removal of any bony structure which remained after the extraction so as to minimize change of shape of the socket wall; and e. inserting and retaining said implant into said socket in surface-to-surface contiguity with a substantial area of the socket wall, whereby to provide for osseointegration of the contiguous areas of the implant and socket wall.

2. A process according to claim 1 in which the following step is accomplished after the implant has become stabilized:

f. applying a crown to said implant.

3. A process according to claim 1 in which the material for said implant is selected from the group consisting of: titanium metal, and a metal not rejected by the human body coated with hydroxylapetite, said hydroxylapetite forming said outer surface.

4. An implant for implantation in a socket in the human jaw from which a tooth has recently been extracted, said implant comprising:

a replica of at least a major part of the root portion of the extracted tooth as it existed immediately after extraction, whose surface is formed of a material not rejected by the human body, and in a surface condition subject to osseointegration.

5. An implant according to claim 4 in which the surface material is selected from the group consisting of titanium metal, and a metal not rejected by the human body coated with hydroxylapetite.

6. An implant according to claim 4 in which said replica of said major part includes a plurality of grooves to encourage retention of the implant.

7. An implant according to claim 4 in which said replica includes an internally threaded bore to receive the threaded end of a headed bolt for holding a crown to the implant.

8. An implant according to claim 4 in which said replica includes a passage therethrough to encompass retention of the implant by ingrowth.

9. An implant according to claim 4 in which said implant is made entirely of titanium metal.

* * * * *

UNITED STATES PATENT AND TRADEMARK OFFICE
CERTIFICATE OF CORRECTION

PATENT NO. : 5,004,422

DATED : 4/2/91

INVENTOR(S) : Robert H. Propper

It is certified that error appears in the above-identified patent and that said Letters Patent is hereby corrected as shown below:

Column 1, line 39, change "osteointegration to --Osseointegration--.

Column 3, line 61, change "3" to --4--.

Column 3, line 66, after "socket" insert --15--.

Figure 6:
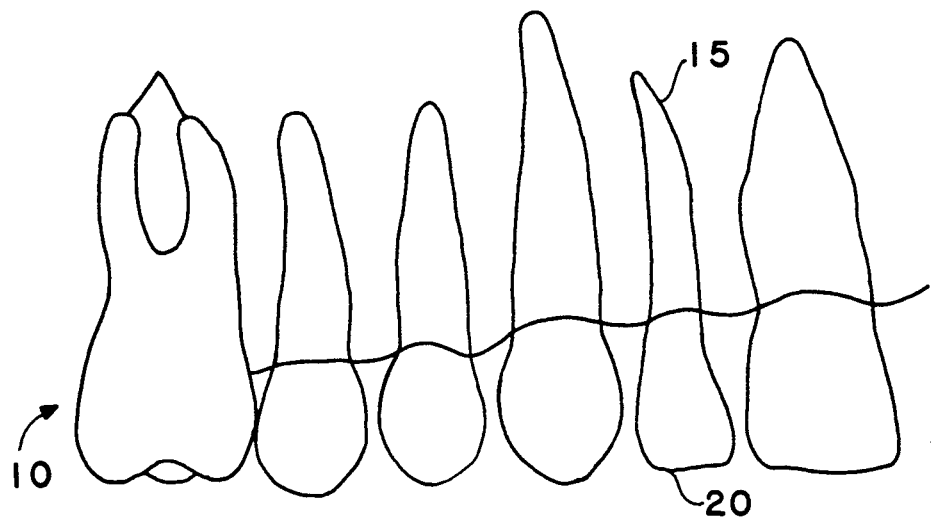
FIG. 6 shows a crown, later placed on the stable implant.

Column 4, line 4, between "it" and the comma, insert --(Fig. 6)--.

Column 4, line 11, change "4" to --7--.

Column 6, line 18, (claim 8) change "encompass" to --encourage--.

Signed and Sealed this

Thirteenth Day of October, 1992

Attest:

DOUGLAS B. COMER

Attesting Officer

Acting Commissioner of Patents and Trademarks